(12) United States Patent
Ueno et al.

(10) Patent No.: US 7,795,312 B2
(45) Date of Patent: Sep. 14, 2010

(54) METHOD FOR TREATING ABDOMINAL DISCOMFORT

(75) Inventors: Ryuji Ueno, Montgomery, MD (US); Sachiko Kuno, Montgomery, MD (US)

(73) Assignee: Sucampo AG, Zug (CH)

( * ) Notice: Subject to any disclaimer, the term of this patent is extended or adjusted under 35 U.S.C. 154(b) by 263 days.

(21) Appl. No.: 10/745,689

(22) Filed: Dec. 29, 2003

(65) Prior Publication Data

US 2004/0138308 A1 Jul. 15, 2004

Related U.S. Application Data

(60) Provisional application No. 60/436,462, filed on Dec. 27, 2002, provisional application No. 60/436,463, filed on Dec. 27, 2002.

(51) Int. Cl.
*A61K 31/5575* (2006.01)
(52) U.S. Cl. .................................................. 514/573
(58) Field of Classification Search .................. None
See application file for complete search history.

(56) References Cited

U.S. PATENT DOCUMENTS

| | | | |
|---|---|---|---|
| 4,158,062 A | 6/1979 | Caton et al. | |
| 5,164,415 A | 11/1992 | Ueno | |
| 5,284,858 A | 2/1994 | Ueno et al. | |
| 5,317,032 A | 5/1994 | Ueno et al. | |
| 6,046,239 A * | 4/2000 | Lennox et al. | 514/563 |
| 6,414,016 B1 | 7/2002 | Ueno | |
| 6,492,417 B1 | 12/2002 | Sharif et al. | |
| 6,583,174 B1 | 6/2003 | Ueno et al. | |
| 7,064,148 B2 * | 6/2006 | Ueno et al. | 514/573 |

FOREIGN PATENT DOCUMENTS

| | | |
|---|---|---|
| EP | 0 978 284 A1 | 2/2000 |
| JP | 2-32055 A | 2/1990 |
| WO | WO 01/76593 A2 | 10/2001 |
| WO | WO 02/089812 A1 | 11/2002 |
| WO | WO 02/094274 A1 | 11/2002 |
| WO | WO 03/030912 A1 | 4/2003 |
| WO | WO 03/041716 A1 | 5/2003 |
| WO | WO 03/043639 A2 | 5/2003 |

OTHER PUBLICATIONS

The Merck Index (1999), 17$^{th}$ edition, pp. 312-315.*
Johnson et al., Gastroenterology, 124(Suppl. 1) (Apr. 3, 2003), pp. 48.*
Johanson J F et al: "Efficacy and Safety of a Novel Compound, RU-0211, for the Treatment of Constipation"; Gastroenterology, W.B. Saunders Company, Philadelphia, US, vol. 122, No. 4, Suppl 1, Apr. 2002, p. A315.
Abstract of NZ 531503 to Sucampo AG, invented by Ryuji Ueno and John Cuppoletti, published on Jan. 27, 2006.
Locke, G. Richard III, "The Epidemiology of Functional Gastrointestinal Disorders in North America," Gastroenterology Clinics of North America, Mar. 1996, vol. 25, No. 1, pp. 1-20.
Hyams, Jeffrey S., "Functional Gastrointestinal Disorders," Current Opinion in Pediatrics 1999, 1999, vol. 11, No. 5, pp. 375-378.
Dunphy et al., "Drug Treatment Options for Irritable Bowel Syndrome: Managing for Success," Drugs and Aging, Jan. 2001, vol. 18, No. 3, pp. 201-211.

* cited by examiner

*Primary Examiner*—Phyllis G. Spivack
(74) *Attorney, Agent, or Firm*—Sughrue Mion, PLLC

(57) ABSTRACT

A method for treating irritable bowel syndrome in a mammalian subject includes administering an effective amount of 13,14-dihydro-15-keto-16,16-difluoro-18-methyl-prostaglandin $E_1$ or 13,14-dihydro-15-keto-16,16-difluoro-prostaglandin $E_1$, or a salt, ether, ester or amide thereof, to the subject. A method for treating abdominal discomfort associated with irritable bowel syndrome in a mammalian subject includes administering an effective amount of 13,14-dihydro-15-keto-16,16-difluoro-18-methyl-prostaglandin $E_1$ or 13,14-dihydro-15-keto-16,16-difluoro-prostaglandin $E_1$, or a salt, ether, ester or amide thereof, to the subject.

22 Claims, No Drawings

METHOD FOR TREATING ABDOMINAL DISCOMFORT

CROSS-REFERENCE TO RELATED APPLICATIONS

This application claims the benefit of provisional application Nos. 60/436,462 and 60/436,463 both filed Dec. 27, 2002, the contents of which are incorporated herein by reference in their entireties.

TECHNICAL FIELD

The present invention relates to a method for treating abdominal discomfort with a chloride channel opener, especially, a prostaglandin compound.

Further, the present invention relates to a method for treating functional gastrointestinal disorders with a chloride channel opener, especially, a prostaglandin compound.

BACKGROUND ART

Abdominal indefinite complaint or abdominal discomfort is most often experienced in our daily lives, and it includes heartburn, nausea, emesis, anorexia, epigastric pain, abdominal bloating, chronic abdominal pain, abdominal discomfort, abnormal bowel movement such as constipation and diarrhea and the like. Various disorders may cause abdominal discomfort. It is also known that abdominal discomfort may also occur as a side effect of drug, medication or surgical procedure. However, it is not yet known as to the drug that may be used for safely and effectively treating abdominal discomfort.

Patients having functional gastrointestinal disorders often report abdominal discomfort. Functional gastrointestinal disorders are characterized by chronic or recurrent gastrointestinal symptoms which are not explained by any organic, i.e. structural or biochemical, abnormality. In general, functional disorders should be distinguished from morphological or organic disorders in which the organ structures have been abnormally changed. An organic disorder may accompany functional abnormality of organs but it is surely possible to diagnose if there is any underlying organic abnormality.

Stress may effect on various organs in various ways, and the typical example of such organs is gastrointestinal tract. The interaction among stress-brain-gastrointestinal organ is called brain-gut axis, and now a days, it draws great interest of the art. In the field of clinical medicine, a group of functional disorders in which the brain-gut axis plays a central role of the pathology is called functional gastrointestinal disorders.

Typical examples of functional gastrointestinal disorders include irritable bowel syndrome (IBS) and functional dyspepsia (FD). These terms are not used for exclusively determining the nature of separate disorders but most commonly used for expressing various overlapping symptoms manifested in the upper and lower gastrointestinal tracts.

IBS is an archetype disorder of functional gastrointestinal disorders with no underlying organic abnormality. IBS patient reports continued lower gastrointestinal symptoms such as abnormal bowel movement, abdominal pain, abdominal bloating and abdominal discomfort, as well as upper gastrointestinal symptoms such as epigastric pain, hypochondriac pain, nausea, anorexia, borborygmus, vomiting, belching and heartburn.

FD patient has no underlying organic disorder such as ulcer and reports continued upper gastrointestinal tract symptoms such as abdominal pain, nausea, anorexia and slow digestion. The term "dyspepsia" means chronic or repetitious pain or discomfort mainly occurring in epigastric region. Up to 60% of the dyspepsia patients have no underlying organic disorder and are diagnosed as FD.

As explained above, functional gastrointestinal disorders are a group of disorders in which the gastrointestinal symptoms continue for a long period or by repeating a period of recrudescence and palliation without clear organic abnormalities. No systematic method has been established for treating such disorder.

Prostaglandins (hereinafter, referred to as PG(s)) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

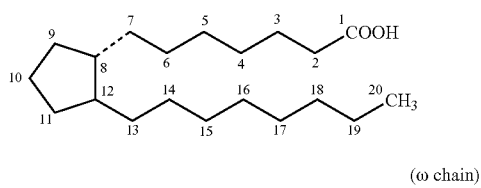

On the other hand, some of synthetic analogues of primary PGs have modified skeletons. The primary PGs are classified to PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:

Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9-position, into α type (the hydroxyl group is an α-configuration) and β type (the hydroxyl group is a β-configuration).

$PGE_1$ and $PGE_2$ and $PGE_3$ are known to have vasodilation, hypotension, gastric secretion decreasing, intestinal tract movement enhancement, uterine contraction, diurectic, bronchodilation and anti ulcer activities. $PGF_{1\alpha}$, $PGF_{2\alpha}$ and $PGF_{3\alpha}$ have been known to have hypertension, vasoconstriction, intestinal tract movement enhancement, uterine contraction, lutein body atrophy and bronchoconstriction activities.

The present inventor already found that prostaglandin compounds open chloride channels, especially ClC channels, more especially ClC-2 channel (WO 03/030912, this reference is herein incorporated by reference).

However, it is not known how chloride channel openers and/or prostaglandin compounds act on abdominal discomfort, or the functional gastrointestinal disorders.

DISCLOSURE OF THE INVENTION

The present inventor has conducted intensive studies and found that a chloride channel opener, especially prostaglandin compound have a significant effect on abdominal discomfort, especially, on functional gastrointestinal disorders such as IBS and FD, which resulted in the completion of the present invention.

Namely, the present invention relates to a method for treating abdominal discomfort in a mammalian subject, which comprises administration of an effective amount of a chloride channel opener, especially ClC channel opener, more especially ClC-2 opener such as prostaglandin compound to the subject.

The present invention further relates to a pharmaceutical composition for treating abdominal discomfort in a mammalian subject, which comprises an effective amount of a chloride channel opener, especially ClC channel opener, more especially ClC-2 channel opener such as prostaglandin compound.

Further more, the present invention relates to a use of a chloride channel opener, especially ClC channel opener, more especially ClC-2 channel opener such as prostaglandin compound for manufacturing a pharmaceutical composition for treating abdominal discomfort in a mammalian subject.

Another embodiment of the present invention relates to a method for treating functional gastrointestinal disorders in a mammalian subject, which comprises administration of an effective amount of a chloride channel opener, especially ClC channel opener, more especially ClC-2 channel opener such as prostaglandin compound to the subject.

The present invention further relates to a pharmaceutical composition for treating functional gastrointestinal disorders in a mammalian subject, which comprises an effective amount of a chloride channel opener, especially ClC channel opener, more especially ClC-2 channel opener such as prostaglandin compound.

Further more, the present invention relates to a use of a chloride channel opener, especially ClC channel operator, more especially ClC-2 channel such as prostaglandin compound for manufacturing a pharmaceutical composition for treating functional gastrointestinal disorders in a mammalian subject.

DETAILED DESCRIPTION OF THE INVENTION

The chloride channel opener used in the present invention is not particularly limited and may be any compound as far as it has a chloride channel opening activity. The chloride channel opening activity may be confirmed by measuring the increase of chloride-ion flows through a chloride channel in a cell membrane from inside to outside of the cell or in the opposite direction. For instance, it is possible to carry out a screening for a compound having chloride channel opening activity by using a known assay strategy such as the patch clamp. Preferred chloride channel opener is a ClC channel opener, especially a ClC-2 channel opener.

Examples of compounds having the opening activity of a ClC-2 channel include cyclooxygenase inhibitor, nonsteroidal anti-inflammatory agent (e.g. ibuprofen and ebselen), protein kinase A, oleic acid, elaidic acid, arachiodonic acid, cell growth factor (e.g., TGFα (transforming growth factor-α) and KGF (keratinocyte growth factor)), benzimidazole derivative and prostaglandin compound. Preferred compound of the present invention is a prostaglandin compound.

The nomenclature of the prostaglandin compounds used herein is based on the numbering system of the prostanoic acid represented in the above formula (A).

The formula (A) shows a basic skeleton of the C-20 carbon atoms, but the present invention is not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification, these terms also include those having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply names as 9- or 11-dehydroxy-PG compound.

As stated above, the nomenclature of the PG compounds is based on the prostanoic acid skeleton. However, in case the compound has a similar partial structure as a prostaglandin, the abbreviation of "PG" may be used. Thus, a PG compound of which α-chain is extended by two carbon atoms, that is, having 9 carbon atoms in the α-chain is named as 2-decarboxy-2-(2-carboxyethyl)-PG compound. Similarly, a PG compound having 11 carbon atoms in the α-chain is named as 2-decarboxy-2-(4-carboxybutyl)-PG compound. Further, a PG compound of which ω-chain is extended by two carbon atoms, that is, having 10 carbon atoms in the ω-chain is named as 20-ethyl-PG compound. These compounds, however, may also be named according to the IUPAC nomenclatures.

Examples of the analogs (including substituted derivative) or derivatives include a PG compound of which carboxy group at the end of α-chain is esterified; a compound of which α-chain is extended; physiologically acceptable salt thereof; a compound having a double bond at 2-3 position or a triple bond at position 5-6, a compound having substituent(s) at position 3, 5, 6, 16, 17, 18, 19 and/or 20; and a compound having lower alkyl or a hydroxy (lower) alkyl group at position 9 and/or 11 in place of the hydroxy group.

According to the present invention, preferred substituents at position 3, 17, 18 and/or 19 include alkyl having 1-4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluoromethylphenoxy. Preferred substituents at position 20 include saturated or unsaturated lower alkyl such as C1-4 alkyl, lower alkoxy such as C1-4 alkoxy, and lower alkoxy alkyl such as C1-4 alkoxy-C1-4 alkyl. Preferred substituents at position 5 include halogen atoms such as chlorine and fluorine. Preferred substituents at position 6 include an oxo group forming a carbonyl group. Stereochemistry of PGs having hydroxy, lower alkyl or hydroxy(lower)alkyl substituent at position 9 and/or 11 may be α, β or a mixture thereof.

Further, the above analogs or derivatives may be compounds having an alkoxy, cycloalkyl, cycloalkyloxy, phenoxy or phenyl group at the end of the ω-chain where the chain is shorter than the primary PGs.

A preferred compounds used in the present invention is represented by the formula (I):

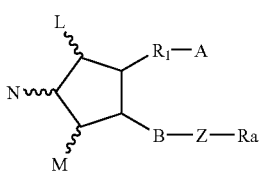

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —CH$_3$, or —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

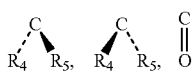

or single bond wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group.

A preferred compound used in the present invention is represented by the formula (II):

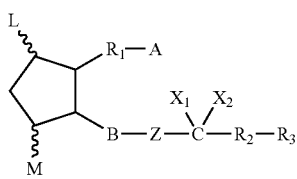

wherein L and M are hydrogen, hydroxy, halogen, lower alkyl, hydroxy(lower)alkyl, lower alkanoyloxy or oxo, wherein at least one of L and M is a group other than hydrogen, and the five-membered ring may have one or more double bonds;

A is —CH$_3$, or —CH$_2$OH, —COCH$_2$OH, —COOH or a functional derivative thereof;

B is a single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

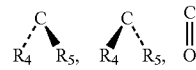

or single bond wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

X$_1$ and X$_2$ are hydrogen, lower alkyl, or halogen;

R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur;

R$_2$ is a single bond or lower alkylene; and

R$_3$ is lower alkyl, lower alkoxy, lower alkanoyloxy, cyclo(lower)alkyl, cyclo(lower)alkyloxy, aryl, aryloxy, heterocyclic group or heterocyclic-oxy group.

In the above formula, the term "unsaturated" in the definitions for R$_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene. The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO-O—, wherein RCO- is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO-, wherein Ar is aryl as defined above. The term "heterocyclic group" may include mono- to tri-cyclic, preferably monocyclic hetercyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO-, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl- monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A mean a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonylamide and tolylsulfonylamide.

Preferred examples of L and M include hydroxy and oxo, and especially, M is hydroxy and L is oxo which as a 5-membered ring structure of, so called, PGE type. Preferred example of A is —COOH, its pharmaceutically acceptable salt, ester or amide thereof.

Preferred example of $X_1$ and $X_2$ is fluorine, so called 16,16-difluoro type.

Preferred $R_1$ is a hydrocarbon residue containing 1-10 carbon atoms, preferably 6-10 carbon atoms. Further, at least one carbon atom in the alipahtic hydrocarbon is optionally substituted by oxygen, nitrogen or sulfur. Examples of $R_1$ include, for example, the following groups:

—$CH_2$—$CH_2$—$CH_2$—$CH_2$—$CH_2$—$CH_2$—,
—$CH_2$—CH=CH—$CH_2$—$CH_2$—$CH_2$—,
—$CH_2$—$CH_2$—$CH_2$—$CH_2$—CH=CH—,
—$CH_2$—C≡C—$CH_2$—$CH_2$—$CH_2$—,
—$CH_2$—$CH_2$—$CH_2$—$CH_2$—O—$CH_2$—,
—$CH_2$—CH=CH—$CH_2$—O—$CH_2$—,
—$CH_2$—C≡C—$CH_2$—O—$CH_2$—,
—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—,
—$CH_2$—$CH_2$—$CH_2$—$CH_2$—$CH_2$—CH=CH—,
—$CH_2$—C≡C—$CH_2$—$CH_2$—$CH_2$—$CH_2$—,
—$CH_2$—$CH_2$—$CH_2$—$CH_2$—$CH_2$—CH($CH_3$)—$CH_2$—,
—$CH_2$—$CH_2$—$CH_2$—$CH_2$—CH($CH_3$)—$CH_2$—,
—$CH_2$—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—$CH_2$—,
—$CH_2$—$CH_2$—$CH_2$—$CH_2$—$CH_2$—$CH_2$—CH=CH—,
—$CH_2$—C≡C—$CH_2$—$CH_2$—$CH_2$—$CH_2$—$CH_2$—, and
—$CH_2$—$CH_2$—$CH_2$—$CH_2$—$CH_2$—$CH_2$—CH($CH_3$)—$CH_2$—.

Preferred Ra is a hydrocarbon containing 1-10 carbon atoms, more preferably, 1-8 carbon atoms. Ra may have one or two side chains having one carbon atom.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

In the present invention, the PG compound which is dihydro between 13 and 14, and keto (=O) at 15 position may be in the keto-hemiacetal equilibrium by formation of a hemiacetal between hydroxy at position 11 and keto at position 15.

For example, it has been revealed that when both of $X_1$ and $X_2$ are halogen atoms, especially, fluorine atoms, the compound contains a tautomeric isomer, bicyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the 15-keto-PG compounds used in the invention include the bicyclic compound and analogs or derivative thereof.

The bicyclic compound is represented by the formula (III)

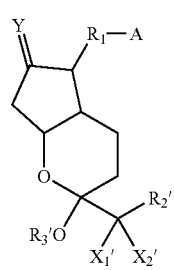

(III)

wherein, A is $-CH_3$, or $-CH_2OH$, $-COCH_2OH$, $-COOH$ or a functional derivative thereof;

$X_1'$ and $X_2'$ are hydrogen, lower alkyl, or halogen;

Y is

wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time.

$R_1$ is a saturated or unsaturated divalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and $R_2'$ is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group.

$R_3'$ is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the hemiacetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073, 569, 5,166,174, 5,221,763, 5,212,324, 5,739,161 and 6,242, 485 (these cited references are herein incorporated by reference).

The term "chloride or ClC or ClC-2 channel opener" used herein includes the compound which activates, promotes or modulates the $Cl^-$ current, $Cl^-$ secretion or $Cl^-$ transport by opening chloride or ClC or ClC-2 channel.

According to the present invention a mammalian subject may be treated by the instant invention by administering the compound used in the present invention. The subject may be any mammalian subject including a human. The compound may be applied systemically or topically. Usually, the compound may be administered by oral administration, intravenous injection (including infusion), subcutaneous injection, intra rectal administration, intra vaginal administration, transdermal administration and the like. The dose may vary depending on the strain of the animal, age, body weight, symptom to be treated, desired therapeutic effect, administration route, term of treatment and the like. A satisfactory effect can be obtained by systemic administration 1-4 times per day or continuous administration at the amount of 0.001-1000 µg/kg per day, more preferably 0.01-100 µg/kg, most preferably 0.1-10 µg/kg.

A typical treatment regimen entails administering to a human patient a composition containing from about 18 to about 30 µg of active ingredient according to the invention from one to three times daily, with about 24 µg two times per day being preferred. The composition for the oral administration may be administered with or without food and/or water.

The compound may preferably be formulated in a pharmaceutical composition suitable for administration in a conventional manner. The composition may be those suitable for oral administration, injection or perfusion as well as it may be an external agent, suppository or pessary.

The composition of the present invention may further contain physiologically acceptable additives. Said additives may include the ingredients used with the present compounds such as excipient, diluent, filler, resolvent, lubricant, adjuvant, binder, disintegrator, coating agent, cupsulating agent, ointment base, suppository base, aerozoling agent, emulsifier, dispersing agent, suspending agent, thickener, tonicity agent, buffering agent, soothing agent, preservative, antioxidant, corrigent, flavor, colorant a functional material such as cyclodextrin and biodegradable polymer, stabilizer. The additives are well known to the art and may be selected from those described in general reference books of pharmaceutics.

The amount of the above-defined compound in the composition of the invention may vary depending on the formulation of the composition, and may generally be 0.00001-10.0 wt %, more preferably 0.0001-1.0 wt %, most preferably 0.001-0.1%.

Examples of solid compositions for oral administration include tablets, troches, sublingual tablets, capsules, pills, powders, granules and the like. The solid composition may be prepared by mixing one or more active ingredients with at least one inactive diluent. The composition may further contain additives other than the inactive diluents, for example, a lubricant, a disintegrator and a stabilizer. Tablets and pills may be coated with an enteric or gastroenteric film, if necessary. They may be covered with two or more layers. They may also be absorbed to a sustained release material, or microcapsulated. Additionally, the compositions may be capsulated by means of an easily degradable material such as gelatin. They may be further dissolved in an appropriate solvent such as fatty acid or its mono, di or triglyceride to be a soft capsule. Sublingual tablet may be used in need of fast-acting property.

Examples of liquid compositions for oral administration include emulsions, solutions, suspensions, syrups and elixirs and the like. Said composition may further contain a conventionally used inactive diluents e.g. purified water or ethyl alcohol. The composition may contain additives other than the inactive diluents such as adjuvant e.g. wetting agents and suspending agents, sweeteners, flavors, fragrance and preservatives.

The composition of the present invention may be in the form of spraying composition, which contains one or more active ingredients and may be prepared according to a known method.

Examples of the injectable compositions of the present invention for parenteral administration include sterile aqueous or non-aqueous solutions, suspensions and emulsions. Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization. The injectable composition may also be provided as a sterilized powder composition to be dissolved in a sterilized solvent for injection before use.

The present external agent includes all the external preparations used in the fields of dermatology and otolaryngology, which includes ointment, cream, lotion and spray.

Another form of the present invention is suppository or pessary, which may be prepared by mixing active ingredients into a conventional base such as cacao butter that softens at body temperature, and nonionic surfactants having suitable softening temperatures may be used to improve absorbability.

The term "treatment" used herein includes any means of control such as prevention, care, relief of the condition, attenuation of the condition and arrest of progression.

The term "abdominal discomfort" used herein includes any abdominal discomfort involved or being associated with any type of condition and/or diseases, or caused by drugs, medications or surgical procedures.

In the present specification and claims, "treatment of abdominal discomfort" or "treating abdominal discomfort" includes to relieve or to eliminate the abdominal discomfort. In addition, "treatment of functional gastrointestinal disorder" or "treating functional gastrointestinal disorder" covers to relieve or to eliminate abdominal discomfort which is associated with functional gastrointestinal disorders.

One of the typical disorders being accompanied by abdominal discomfort includes functional gastrointestinal disorders. Examples of the functional gastrointestinal disorders include irritable bowel syndrome and functional dyspepsia.

The pharmaceutical composition of the present invention may further contain other pharmacological ingredients as far as they do not contradict the purpose of the present invention.

The further details of the present invention will follow with reference to test examples, which, however, are not intended to limit the present invention.

EXAMPLE 1

Methods

Patients with irritable bowel syndrome (IBS) were randomly allocated to the following two treatment groups.
Group 1: Test substance (13,14-dihydro-15-keto-16,16-difluoro-$PGE_1$) 48 µg total (24 µg/breakfast+24 µg/dinner)
Group 2: Matching placebo (placebo/breakfast+placebo/dinner)

Each group underwent two weeks washout period and then began to administer oral test substance (capsules) or placebo (capsules) daily for 4 weeks. Test substance or placebo was taken two times a day (b.i.d) at breakfast with food and at least 8 ounces of water and at dinner with food and at least 8 ounces of water. Patients were asked to evaluate abdominal discomfort upon waking in the morning, using a 5-point scale (Score: 0=absent, 1=mild, 2=moderate, 3=severe, 4=very severe) at 4 weeks after the initiation of the treatments.

Results

As shown in Table 1, test substance of this invention significantly improved the abdominal discomfort in the patients with IBS.

TABLE 1

Effect of test substance on abdominal discomfort in patients with IBS

| | Abdominal discomfort score, Mean ± SD (N) | |
|---|---|---|
| Week | Placebo | Test Substance |
| Baseline | 2.31 ± 0.788 (26) | 2.25 ± 0.803 (32) |
| Week 4 | 2.19 ± 0.895 (26) | 1.48 ± 1.029** (31) |

Test substance: 13,14-dihydro-15-keto-16,16-difluoro-$PGE_1$
**$p < 0.01$ (van Elteren test stratified by center)

EXAMPLE 2

Method

Patients with occasional constipation were randomly allocated to the following two treatment groups.
Group 1: Test substance (13,14-dihydro-15-keto-16,16-difluoro-PGE1) 48 µg total (24 µg/breakfast+24 µg/dinner)
Group 2: Matching placebo (placebo/breakfast+placebo/dinner)

Each group underwent two weeks washout period and then began to administer oral test substance (capsules) or placebo (capsules) daily for 4 weeks. During the washout period, the patient's bowel habit was documented to confirm the existence of constipation. Constipation is defined as, on average, less than three spontaneous bowel movements per week. All existing laxative medication was withdrawn at the start of the washout period and the patients were instructed not to change their diet or lifestyle during the study.

Test substance or placebo was taken orally for a total treatment period of 4 weeks; it was taken two times a day (b.i.d) at breakfast with food and at least 8 ounces of water and at dinner with food and at least 8 ounces of water.

The patients were asked to evaluate abdominal discomfort upon waking in the morning, using a 5-point scale (Score: 0=absent, 1=mild, 2=moderate, 3=severe, 4=very severe) at 2 and 4 weeks after the initiation of the treatments.

Results

As shown in Table 2, test substance of this invention significantly improved the abdominal discomfort in patients with constipation.

TABLE 2

Effect of test substance on abdominal discomfort in patients with constipation

| | Abdominal discomfort score, Mean ± SD (N) | |
|---|---|---|
| | Placebo | Test Substance |
| Week 2 | 1.41 ± 1.035 (122) | 1.09 ± 1.047* (116) |
| Week 3 | 1.64 ± 1.114 (122) | 1.27 ± 1.057* (117) |
| Week 4 | 1.52 ± 1.038 (122) | 1.22 ± 1.060* (117) |

Test substance: 13,14-dihydro-15-keto-16,16-difluoro-PGE$_1$
*p < 0.05 (van Elteren test stratified by center)

EXAMPLE 3

Methods

Patients with irritable bowel syndrome (IBS) were randomly allocated to the following two treatment groups.

Group 1: Test substance (13,14-dihydro-15-keto-16,16-difluoro-PGE$_1$) 48 μg total (24 μg/breakfast+24 μg/dinner)

Group 2: Matching placebo (placebo/breakfast+placebo/dinner)

Each group underwent two weeks washout period and then began to administer oral test substance (capsules) or placebo (capsules) daily for 4 weeks. Test substance or placebo was taken two times a day (b.i.d) at breakfast with food and at least 8 ounces of water and at dinner with food and at least 8 ounces of water. The patients were asked to evaluate abdominal bloating upon waking in the morning, using a 5-point scale (Score: 0=absent, 1=mild, 2=moderate, 3=severe, 4=very severe) at 4 weeks after the initiation of the treatments.

Results

As shown in Table 3, test substance of this invention significantly improved the abdominal bloating in patients with IBS.

TABLE 3

Effect of test substance on abdominal bloating in patients with IBS

| | Abdominal bloating score, Mean ± SD (N) | |
|---|---|---|
| Week | Placebo | Test Substance |
| Baseline | 2.46 ± 0.859 (26) | 2.50 ± 0.916 (32) |
| Week 4 | 2.42 ± 0.945 (26) | 1.74 ± 0.999** (31) |

Test substance: 13,14-dihydro-15-keto-16,16-difluoro-PGE$_1$
**p < 0.01 (van Elteren test stratified by center)

EXAMPLE 4

Methods

Patients with irritable bowel syndrome (IBS) exhibiting dyschezia were randomly allocated to the following two treatment groups.

Group 1: Test substance (13,14-dihydro-15-keto-16,16-difluoro-PGE$_1$) 48 μg total (24 μg/breakfast+24 μg/dinner)

Group 2: Matching placebo (placebo/breakfast+placebo/dinner)

Each group underwent two weeks washout period and then began to administer oral test substance (capsules) or placebo (capsules) daily for 4 weeks. Test substance or placebo was taken two times a day (b.i.d) at breakfast with food and at least 8 ounces of water and at dinner with food and at least 8 ounces of water. After 3 consecutive days of not having spontaneous bowel movement, the investigator could prescribe to the patient 10 mg bisacodyl suppository as a rescue medication. If this was not effective, Fleet® enema could be used. During the study period, each patient documented bowel activity. A spontaneous bowel movement was defined as any bowel movement except for that occurred within 24 hours after the rescue medication. Frequency of spontaneous bowel movements at Baseline, Weeks 1, 2, 3 and 4 were analyzed.

Results

As shown in Table 4, test substance of this invention significantly improved the spontaneous bowel movement frequency in patients with IBS exhibiting dyschezia.

TABLE 4

Effect of test substance on spontaneous bowel movement frequency rates in patients with IBS exhibiting dischezia

| | Spontaneous Bowel Movement Frequency Rates, Mean ± SD (N) | |
|---|---|---|
| Week | Placebo | Test Substance |
| Baseline | 1.85 ± 2.310 (26) | 1.43 ± 0.773 (32) |
| Week 1 | 3.58 ± 2.887 (26) | 6.50 ± 4.108** (32) |
| Week 2 | 2.84 ± 2.481 (26) | 5.58 ± 4.003** (32) |
| Week 3 | 2.30 ± 2.170 (26) | 5.93 ± 4.775** (32) |
| Week 4 | 2.21 ± 2.399 (26) | 5.17 ± 4.333* (32) |

Test substance: 13,14-dihydro-15-keto-16,16-difluoro-PGE$_1$
*p < 0.05, ** p < 0.01 (van Elteren test stratified by center)

What is claimed is:

1. A method for treating irritable bowel syndrome in a mammalian subject, which comprises administering an effective amount of 13,14-dihydro-15-keto-16,16-difluoro-18-methyl-prostaglandin E$_1$, or a salt, ether, ester or amide thereof, to the subject.

2. The method as described in claim 1, which comprises administering an effective amount of 13,14-dihydro-15-keto-16,16-difluoro-18-methyl-prostaglandin E$_1$, or a pharmaceutically acceptable salt, ester or amide thereof.

3. The method as described in claim 1, which comprises systemic administration 1-4 times per day or continuous administration in the amount of 0.01-100 μg/kg per day or a 13,14-dihydro-15-keto-16,16-difluoro-18-methyl-prostaglandin E$_1$ compound.

4. A method for treating as described in claim 2, wherein the administration is in the amount of 0.1-10 μg/kg per day.

5. The method as described in claim 1, which comprises systemic administration 1-4 times per day or continuous administration at the amount of 0.01-100 μg/kg per day.

6. The method as described in claim 5, wherein the administration is at the amount of 0.1-10 μg/kg per day.

7. A method for treating irritable bowel syndrome in a mammalian subject, which comprises administering an effective amount of 13,14-dihydro-15-keto-16,16-difluoro prostaglandin $E_1$ or a salt, ether, ester or amide thereof, to the subject.

8. The method as described in claim 7, which comprises administering an effective amount of 13,14-dihydro-15-keto-16,16-difluoro-prostaglandin $E_1$, or a pharmaceutically acceptable salt, ester or amide thereof.

9. The method for treating irritable bowel syndrome in a as described in claim 8, which comprises systemic administration 1-4 times per day or continuous administration in the amount of 0.01-100 μg/kg per day.

10. The method as described in claim 8, wherein the administration is in the amount of 0.1-10 μg/kg per day.

11. The method as described in claim 7, which comprises systemic administration 1-4 times per day or continuous administration at the amount of 0.01-100 μg/kg per day.

12. The method as described in claim 7, wherein the administration is at the amount of 0.1-10 μg/kg per day.

13. A method for treating abdominal discomfort associated with irritable bowel syndrome in a mammalian subject, which comprises administering an effective amount of 13,14-dihydro-15-keto-16,16-difluoro-18-methyl-prostaglandin $E_1$, or a salt, ether, ester or amide thereof, to the subject.

14. The method as described in claim 13, which comprises administering an effective amount of 13,14-dihydro-15-keto-16,16-difluoro-18-methyl-prostaglandin $E_1$, or a pharmaceutically acceptable salt, ester or amide thereof.

15. The method as described in claim 14, which comprises systemic administration 1-4 times per day or continuous administration in the amount of 0.01-100 μg/kg per day.

16. The method as described in claim 13, which comprises systemic administration 1-4 times per day or continuous administration in the amount of 0.01-100 μg/kg per day.

17. The method as described in claim 13, wherein the administration is in the amount of 0.1-10 μg/kg per day.

18. A method for treating abdominal discomfort associated with irritable bowel syndrome in a mammalian subject, which comprises administering an effective amount of 13,14-dihydro-15-keto-16,16-difluoro prostaglandin $E_1$, or a salt, ether, ester or amide thereof, to the subject.

19. The method as described in claim 18, which comprises administering an effective amount of 13,14-dihydro-15-keto-16,16-difluoro-prostaglandin $E_1$, or a pharmaceutically acceptable salt, ester or amide thereof.

20. The method as described in claim 19, which comprises systemic administration 1-4 times per day or continuous administration in the amount of 0.01-100 μg/kg per day.

21. The method as described in claim 18, which comprises systemic administration 1-4 times per day or continuous administration in the amount of 0.01-100 μg/kg per day.

22. The method as described in claim 18, wherein the administration is in the amount of 0.1-10 μg/kg per day.

* * * * *